United States Patent
Song et al.

(10) Patent No.: US 9,128,013 B2
(45) Date of Patent: Sep. 8, 2015

(54) SAMPLER FOR TAKING SAMPLES FROM MELTS HAVING A MELTING POINT HIGHER THAN 600 ° C. AND METHOD FOR TAKING SAMPLES

(75) Inventors: Lihuan Song, Lommel (BE); Gerrit Broekmans, Paal (BE); Guido Jacobus Neyens, Opoeteren (BE); Dries Beyens, Kinrooi (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 416 days.

(21) Appl. No.: 13/464,019

(22) Filed: May 4, 2012

(65) Prior Publication Data

US 2012/0293798 A1 Nov. 22, 2012

(30) Foreign Application Priority Data

May 18, 2011 (DE) .......................... 10 2011 101 943
Dec. 16, 2011 (DE) .......................... 10 2011 121 183

(51) Int. Cl.
*G01J 3/28* (2006.01)
*G01N 1/12* (2006.01)
*G01N 33/20* (2006.01)

(52) U.S. Cl.
CPC .............. *G01N 1/125* (2013.01); *G01N 33/206* (2013.01)

(58) Field of Classification Search
CPC ................................................... G01N 1/2035
See application file for complete search history.

(56) References Cited

U.S. PATENT DOCUMENTS

| 3,315,529 | A | | 4/1967 | Feichtinger |
| 3,751,986 | A | | 8/1973 | Boron |
| 3,798,974 | A | | 3/1974 | Boron |
| 3,813,944 | A | * | 6/1974 | Ryntz et al. ..................... 374/26 |
| 3,897,689 | A | | 8/1975 | Boron |
| 3,996,803 | A | | 12/1976 | Falk |
| 4,361,053 | A | | 11/1982 | Jones et al. |
| 4,503,716 | A | | 3/1985 | Wuensch |
| 4,566,343 | A | | 1/1986 | Theuwis et al. |
| 4,893,516 | A | | 1/1990 | Knevels |

(Continued)

FOREIGN PATENT DOCUMENTS

| CN | 1096369 A | 12/1994 |
| CN | 2405208 Y | 11/2000 |

(Continued)

OTHER PUBLICATIONS

English translation of an Office Action issued Apr. 1, 2013 in RU Application No. 2012120481.

(Continued)

*Primary Examiner* — Hezron E Williams
*Assistant Examiner* — Mark A Shabman
(74) *Attorney, Agent, or Firm* — Panitch Schwarze Belisario & Nadel LLP

(57) ABSTRACT

A sampler is provided for taking samples from melts having a melting point higher than 600° C., in particular for metal or cryolite melts. The sampler includes a carrier tube having an immersion end and having a sample chamber assembly arranged on the immersion end of the carrier tube. The assembly has an inlet opening and a sample cavity for the melt and is arranged at least partly inside the carrier tube. The sample chamber assembly has on a part of its outer surface a coupling device, arranged inside the carrier tube, for coupling a carrier lance. A method is also provided for taking samples using such a sampler.

20 Claims, 13 Drawing Sheets

(56) References Cited

U.S. PATENT DOCUMENTS

| | | | |
|---|---|---|---|
| 5,415,052 A | 5/1995 | Baerts | |
| 5,577,841 A | 11/1996 | Wall | |
| 5,712,710 A | 1/1998 | Karakus et al. | |
| 5,948,350 A * | 9/1999 | Falk | 266/80 |
| 6,113,669 A | 9/2000 | Vorobeichik et al. | |
| 7,748,258 B2 | 7/2010 | Sattmann | |
| 7,832,294 B2 | 11/2010 | Neyens | |
| 8,001,856 B2 | 8/2011 | Knevels et al. | |

FOREIGN PATENT DOCUMENTS

| | | |
|---|---|---|
| CN | 2608967 Y | 3/2004 |
| DE | 2504583 A1 | 8/1976 |
| DE | 3203505 A1 | 8/1983 |
| DE | 3233677 C1 | 12/1983 |
| DE | 4303687 C1 | 6/1994 |
| DE | 102005060492 B3 | 5/2007 |
| DE | 102006047765 B3 | 12/2007 |
| DE | 102008031390 B4 | 12/2010 |
| EP | 0143498 A2 | 6/1985 |
| EP | 1544591 A2 | 6/2005 |
| GB | 2167326 A | 5/1986 |
| JP | 52-94191 A | 8/1977 |
| JP | 62-30940 A | 2/1987 |
| RU | 2308695 C2 | 10/2007 |
| WO | 2009030206 A2 | 3/2009 |

OTHER PUBLICATIONS

Office Action issued Aug. 29, 2011 in DE Application No. 10 2011 101 943.3.

Office Action issued Feb. 8, 2012 in DE Application No. 10 2011 121 183.0.

Office Action issued Feb. 11, 2014 in AU Application No. 2012202450.

Office Action issued Apr. 28, 2014 in CN Application No. 201210155472.5.

* cited by examiner

SAMPLER FOR TAKING SAMPLES FROM MELTS HAVING A MELTING POINT HIGHER THAN 600° C. AND METHOD FOR TAKING SAMPLES

BACKGROUND OF THE INVENTION

The invention relates to a sampler for taking samples from melts having a melting point higher than 600° C., in particular for metal or cryolite melts, especially iron or steel melts. The sampler comprises a carrier tube having an immersion end and having a sample chamber assembly arranged on the immersion end of the carrier tube. The assembly has an inlet opening and a sample cavity for the melt and is arranged at least partially inside the carrier tube. In addition, the invention relates to a sample chamber assembly for such a sampler and to a method for taking samples using such a sampler.

Numerous samplers for melts, in particular for metal or cryolite melts, are known. For example, German Patent DE 32 33 677 C1 describes a sampler for metal and slag. Here, on the immersion end of a carrier tube there is provided an inlet opening for a sample cavity, which is covered by a protective cap. Similar samplers are known from European patent application EP 1 544 591 A2 or from German published patent application DE 25 04 583 A1.

From German Patent DE 10 2005 060 492 B3 a combination is known of a sampler and sensors for measurement in metal or slag melts. Here, a measurement head is disclosed for accommodating the sensors, additionally having on its immersion end an inlet opening for a sample cavity.

These samplers have in common that the sample cavity is arranged on the immersion end of a carrier tube intended for immersion in the melt, whereby after the taking of the sample and the withdrawal of the carrier tube from the melt, the immersion end with the sample cavity is separated from the carrier tube, and the sample is subsequently removed from the sample cavity and delivered to an analysis device. Further similar arrangements are disclosed, for example, in U.S. Pat. No. 6,113,669.

Carrier tubes are described, inter alia, in European patent application publication EP 143 498 A2 and U.S. Pat. No. 4,893,516. Here it is also disclosed that the carrier tube is attached to a lance for the measurement or taking of samples. The lance serves for the automated machine handling or manual handling of the carrier tube having the sample cavity or the sensors. Using the lance, the carrier tube is immersed in the metal melt and withdrawn from it. The carrier tube having the sampler or sensor equipment is a disposable article, which is disposed of after being used once, while the lance (also designated carrier lance) is used multiple times.

The lance is used not only for the immersion of the carrier tube, but also to transmit signals via the signal cable routed through the lance. The lance is connected to the carrier tube by a so-called coupling piece, wherein signal cables or other functional units may also be integrated in the coupling piece. Corresponding contacts, with whose aid a transmission of signals through a carrier lance takes place, are represented, inter alia, in German Patent DE 10 2005 060 492 B3.

In the known samplers, the removal of the sample from the sample cavity takes place immediately after withdrawal of the carrier tube from the metal melt, whereby the immersion end of the carrier tube and the sample cavity themselves are destroyed while releasing the sample arranged in the sample cavity. For this purpose, the carrier tube can be simply dropped onto the floor next to the melt container, so that the carrier tube, which is damaged anyway during the immersion process and as a rule is made of cardboard, falls apart and releases the sample. Sample cavities for hot melts, such as metal melts, are often formed from two-part sample chamber assemblies, so that the two parts fall apart from one another and release the sample. In particular with high-temperature melts, such as steel melts, the sample itself is still very hot when it is exposed to the ambient air by opening the sample cavity. As a result, the surface of the sample can oxidize, so that a post-treatment of the sample is required before analysis. From German published patent application DE 25 04 583 A1 it is also known to pull the sample chamber assembly out through the protective housing.

BRIEF SUMMARY OF THE INVENTION

An object of the invention is to improve the known samplers, in particular for metal melts or cryolite melts, especially iron or steel melts, and to enable a faster analysis of the samples.

The sampler is characterized in particular in that the sample chamber assembly has on a part of its outer surface a coupling device, arranged inside the carrier tube, for coupling a carrier lance, and that the sample chamber assembly has an inner wall for the sample cavity (i.e., a part immediately surrounding the sample cavity in which the sample is to be obtained) and an outer wall, wherein the outer wall surrounds the inner wall at least partially at a distance therefrom, such that there is a hollow space between the outer wall and the inner wall. The hollow space can be filled with gas, in particular inert gas, or can contain a vacuum. In this way, in the sample chamber assembly there results a kind of double chamber in which the inner chamber is the sample cavity and the outer chamber, surrounding the inner chamber, forms a gas space (or vacuum space).

Here, it is possible to withdraw the sample chamber assembly as a whole, or a part thereof, with the carrier lance from the end of the carrier tube opposite the immersion end, so that a surface of the sample is exposed and accessible for analysis. Because this exposure of the surface can take place either in the carrier tube or outside it, if the entire sample chamber assembly is removed through the carrier tube, the sample can be submitted to analysis under controlled conditions. Here, the removal of the sample or exposure of a sample surface takes place such that it can be delivered immediately for the analysis and without preceding preparation. In this context, the term "sample analysis" is to be understood as the reception of the optical signals necessary for evaluation by a spectrometer (and the evaluation of the signals); from there results a forwarding of the signals to evaluation devices, computers, or the like.

In particular, it is advantageous that the sample chamber assembly have as an inner wall a plurality of parts that directly surround the sample cavity and can be detached from one another, wherein at least one of the parts is arranged inside the carrier tube. In this way, using the carrier lance, at least this part can be removed from the sample through the carrier tube. It is further expedient that the sample chamber assembly or the part of the sample chamber assembly having the coupling device be arranged on the immersion end of the carrier tube, such that the sample chamber assembly or the part having the coupling device can be moved through the interior of the carrier tube to the end opposite the immersion end of the carrier tube, and from there can be withdrawn from the carrier tube.

Preferably, the sample chamber assembly or the part of the sample chamber assembly having the coupling device has a cross-section perpendicular to the longitudinal axis of the carrier tube that is at most as large as the cross-section of the interior of the carrier tube perpendicular to its longitudinal axis. The cross-section of the sample chamber assembly or of the part of the sample chamber assembly having the coupling device is characterized by its silhouette (outlining edge), which must not be allowed to protrude past the cross-section of the inside of the carrier tube at any point, because otherwise a removal of the sample chamber assembly or its part through the carrier tube is not possible or is possible only after tilting with respect to the longitudinal axis, which either prevents success or enables it only with increased effort.

It is expedient that the sample chamber assembly have a first part and a second part, which together surround the sample cavity, and that the carrier tube have a main part, containing the coupling device, and an end part arranged on the immersion end of the carrier tube so as to be detachable from the main part, wherein the first part of the sample chamber assembly is fixed on the main part and the second part of the sample chamber assembly is fixed on the end part of the carrier tube. In this way, it is possible to easily and rapidly disassemble the carrier tube after taking the sample, wherein the parts of the sample chamber assembly are simultaneously detached from one another, so that a part of the sample surface is freely accessible for analysis. The carrier tube need not be broken apart or cut with great effort, because it has a predetermined break point at the point at which the main part and end part are connected.

The end part can be connected to the main part by a press-fit connection or screw connection. Preferably, the end part can be connected to the main part by clamps or staples. In this way, on the one hand a secure connection is ensured for transport and use of the sampler, and on the other hand easy and rapid separation is possible using simple handles or tools. If the sampler additionally has sensors on its immersion end, such as a thermal element or an electrochemical sensor, connecting wires of the sensors are routed through the inside of the carrier tube. When the end part is separated from the main part of the carrier tube, these connecting wires are also separated. Here, predetermined break points or conventional separating mechanisms can be provided, which separate the connecting wires below the sample surface that is to be exposed, i.e. between the sample surface and the immersion end of the sampler. In this way, the connecting wires are prevented from possibly moving onto or across the sample surface that is to be analyzed, which would disturb the analysis.

It is further advantageous that the coupling device be constructed as a snap coupling or bayonet coupling or screw coupling, in order to enable a simple coupling to standard carrier lances. Furthermore, it is expedient that the ratio of the mass of the melt taken up in the sample cavity to the mass of the sample chamber assembly, in particular the inner wall of the sample chamber assembly, without the melt be less than 0.8, preferably at most 0.1. This achieves a rapid cooling of the melt that has flowed into the sample cavity, so that when a sample surface is exposed, the melt has already cooled sufficiently that oxidation is prevented to the greatest extent possible, so that post-treatment of the sample surface is unnecessary.

The sample chamber assembly has an inner wall for the sample cavity and an outer wall, wherein the outer wall surrounds the inner wall at least partially at a distance therefrom, forming a hollow space. The mass ratio can be formed with the aid of the material of the inner wall for the sample cavity. The inner wall of the sample chamber assembly can be made completely or partially of copper, in order to increase the cooling effect. Due to the partial spacing of the outer wall from the inner wall, an inert gas can be introduced into the resulting hollow space, in order to create a non-oxidizing atmosphere in the immediate environment of the sample. The inert gas can preferably be supplied by the coupling device having at least one gas flow channel that runs through the outer wall of the sample chamber assembly or leads up to this wall.

A sample chamber assembly according to an embodiment of the invention for a sampler as described above, having a sample cavity immediately surrounded by an inner wall formed from a plurality of parts, and having an inlet tube connected to the sample cavity for accommodating a sample of a metal melt or cryolite melt, in particular a steel melt, in the sample cavity, wherein the inlet tube opens into the sample cavity with an inlet opening, is characterized in that the ratio V between the mass M (g) of the sample and the material of the inner wall is represented by the following equation:

$$V = \frac{M \times 24000}{m \times c \times \lambda} < 0.15$$

where m is the mass (g) of the inner wall, c is the specific heat capacity (J/kg·° K) and λ is the thermal conductivity (W/m·° K) of the material of the inner wall. Preferably, the ratio V<0.05. This brings about a rapid cooling of the inflowing melt from, for example, more than 1600° C. (in the case of a steel melt) to 200 to 300° C., so that the surface can be made available for analysis without oxidizing. The sample can be, for example, a steel or iron sample. Copper or aluminum, among others, are suitable materials for the inner wall. If necessary, good samples can still be achieved even with a ratio V<0.3.

The sample chamber assembly has a flat shape (for example a circular disk) by its two parts of the inner wall, with a flat, smooth sample surface exposed after removing the one part of the inner wall. The second part of the inner wall, in which the sample at first remains, can have openings through which gas can escape when the sample cavity is filled, or through which gas can be previously suctioned out, forming a vacuum, and if necessary through which an excess of inflowing melt that may be present can exit. The melt exiting through the openings hardens, as does the sample itself, fixing the sample on this second part of the inner wall, so that it can be more easily supplied for analysis. The first part of the inner wall can also have openings for ventilating the sample cavity.

The ratio of sample volume, i.e. volume (in mm³) of the sample cavity to the overall cross-section (in mm²) of the openings leading out from the sample cavity and serving for ventilation is less than 500 mm, preferably less than 100 mm, in order to enable effective ventilation.

The parts of the wall of the sample chamber assembly can be pressed against one another, and thus held together, by springs, in particular spiral springs. The sample chamber assembly advantageously has at least two parts immediately surrounding the sample cavity and detachable from one another.

Preferably, the inlet tube has a reduced cross-section at the inlet opening. Thus, it is constructed as a tube having approximately uniform diameter and cross-section over its length, wherein the cross-section becomes smaller at the inlet opening. The opposite opening, for the flow of the melt into the inlet tube, can also have a reduced cross-section, which is preferably smaller than the cross-section of the inlet opening into the sample cavity. Here, the cross-section of the inlet tube is preferably circular and the opposite opening can have a diameter of approximately 3 mm, while the inlet tube can have a diameter of approximately 8 mm over its length, and the inlet opening into the sample cavity can have a diameter of approximately 6 mm.

The method according to the invention for taking samples from melts having a melt temperature greater than 600° C., in particular for metal melts or cryolite melts, especially for iron or steel melts, using a sampler according to the invention, wherein a carrier lance is pushed into the carrier tube through the end opposite an immersion end of the carrier tube, is characterized in that the carrier lance is coupled to the coupling device of the sample chamber assembly, that subsequently the immersion end of the carrier tube is immersed in the melt and the sample cavity of the sample chamber assembly is filled with melt, that the sample chamber assembly or the part of the sample chamber assembly having the coupling device is then pulled through the carrier tube using the carrier lance and withdrawn from the end of the carrier tube opposite the immersion end, and that after the withdrawal from the carrier tube of the part of the sample chamber assembly having the coupling device, whereby a part of the surface of the sample in the sample chamber assembly enters into direct contact with the surrounding environment of the sample chamber assembly (or with the hollow space situated between the inner wall and the outer wall of the sample chamber assembly), a lance having a spectrometer is pushed into the carrier tube and the surface of the sample is analyzed with the aid of the spectrometer.

An alternative specific embodiment of the method according to the invention for taking samples from melts having a melt temperature greater than 600° C., in particular for metal melts or cryolite melts, especially for iron or steel melts, using a sampler according to the invention, wherein a carrier lance is pushed into the carrier tube through the end opposite an immersion end of the carrier tube, is characterized in that the carrier lance is coupled to the coupling device of the sample chamber assembly, that subsequently the immersion end of the carrier tube is immersed in the melt and the sample cavity of the sample chamber assembly is filled with melt, that the sample chamber assembly or the part of the sample chamber assembly having the coupling device is then pulled through the carrier tube using the carrier lance and withdrawn from the end of the carrier tube opposite the immersion end, and that after the withdrawal from the carrier tube of the part of the sample chamber assembly having the coupling device, whereby a part of the surface of the sample in the sample chamber assembly enters into direct contact with the surrounding environment of the sample chamber assembly (or with the hollow space situated between the inner wall and the outer wall of the sample chamber assembly), a lance having a gripper or manipulator is pushed into the carrier tube, and the gripper or manipulator grasps the sample, removes it from the sample chamber assembly, and pulls it through the carrier tube, withdrawing it from the end of the carrier tube opposite the immersion end.

In this way, the sample remains for a relatively long time in a comparatively well-protected environment and can cool off there until it reaches a temperature at which the sample surface does not immediately oxidize, so that it can be analyzed without further treatment. Relative to melt temperatures of iron or steel melts of more than 1450° C., this cooled temperature is only a few hundred degrees Celsius, for example 200-300° C. Here, analysis takes place in a relatively protected environment without the sample itself having to be removed from the carrier tube. This can be advantageous in particular if the part of the sample chamber assembly not removed using the carrier lance is fastened, for various reasons, to the immersion end of the carrier tube, such that it cannot be removed therefrom without destroying the carrier tube.

Preferably, the sample chamber is delivered to an analysis device after being withdrawn from the carrier tube.

In addition, it can be advantageous that, after the withdrawal from the carrier tube of the part of the sample chamber assembly having the coupling device, wherein a part of the surface of the sample in the sample chamber assembly enters into direct contact with the surrounding environment of the sample chamber assembly (or with the hollow space situated between the inner wall and the outer wall of the sample chamber assembly), the sample be removed from the immersion end of the carrier tube, wherein it is either pulled through the immersion end or the immersion end or a part thereof with the sample is removed from the carrier tube. This can make sense if, due to particularities of the construction or operation, an analysis inside the carrier tube or a removal of the sample through the carrier tube is not possible or practical. It is advantageous that the sample be delivered to an analysis device outside the carrier tube.

It is further advantageous that the carrier tube be pulled out of the melt before the withdrawal from the carrier tube of the sample chamber assembly or of the part of the sample chamber assembly having the coupling device. In addition, it can make sense for an inert gas to be conducted to the sample chamber assembly or into a hollow space of the sample chamber assembly during and/or after the taking of the sample. In this way, oxygen is prevented from entering the sample, so that even at high temperatures the sample cannot oxidize, and an analysis of the sample is possible without additional post-treatment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
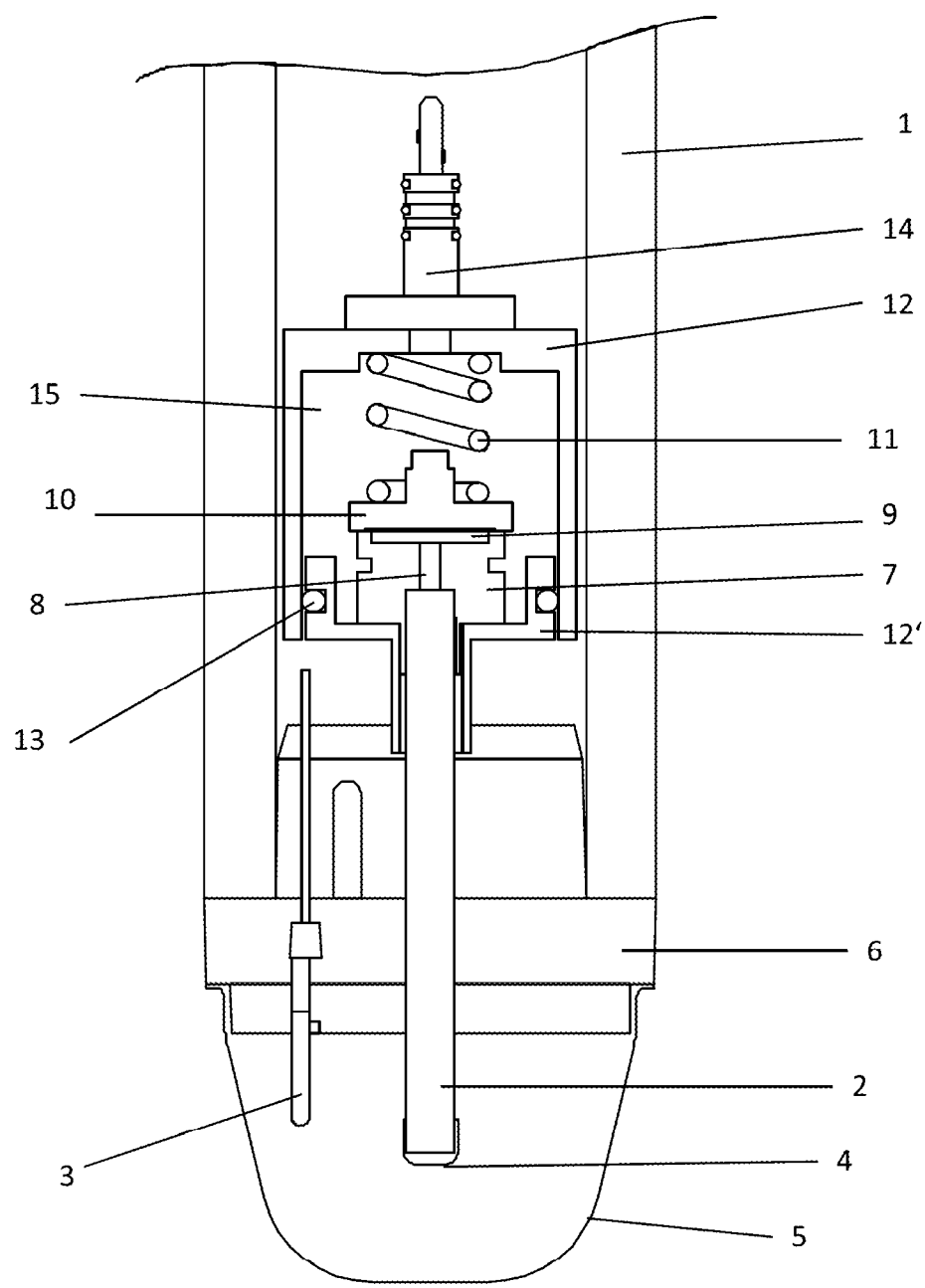
FIG. 1 is a schematic, longitudinal, cross-sectional representation of a sampler according to an embodiment of the invention.

FIG. 1 shows a sectional representation of the immersion end of the sampler. The inlet tube 2 for the metal melt sample and a thermal element 3 open at the immersion end of carrier tube 1. Inlet tube 2 is protected by a metal cap 4. This cap and the outer protective cap 5, made of metal, prevent damage during transport and damage when the sampler penetrates through a slag layer, before the opening of inlet tube 2 is freed after immersion in a metal melt, for example a steel melt. Thermal element 3 and inlet tube 2 are fixed in a refractory body 6. Inlet tube 2 opens into a cooling body 7, through whose pass-through opening 8 the metal melt penetrates into sample cavity 9. This cavity is closed at its upper side (seen in the direction of immersion) by an upper cooling body 10. Cooling bodies 7,10 can be made of copper, so that a faster flow of heat from the captured sample takes place and the sample is quickly cooled. Lower cooling body 7 and upper cooling body 10 together form the inner wall of the sample chamber assembly. Sample cavity 9 itself has a thickness of approximately 2 mm and a diameter of approximately 28 mm.

Preferably, the ratio of the mass of the steel melt flowed into sample cavity 9 to the mass of cooling bodies 7,10 is less than 0.1, so that the metal melt hardens and cools very quickly to a temperature of approximately 200° C. Cooling bodies 7,10 are made of copper. Here, with the relative size shown in the Figures, there results a ratio V of approximately 0.0167. Upper cooling body 10 is pressed against lower cooling body 7 by a spiral spring, so that sample cavity 9 is sealed. The counter surface of spiral spring 11 is formed by outer wall 12,12' of the sample chamber assembly. Lower part 12' of the outer wall has a pass-through opening for inlet tube 2 and forms the lower counter surface for spiral spring 11 and for cooling bodies 7,10. Cooling bodies 7,10 form the inner wall of the sample chamber assembly. The two parts of the outer wall 12,12' are fixed to one another and are sealed by a seal 13.

On the upper side of upper part 12 of the outer wall there is arranged a coupling device 14 for a carrier lance, not shown in the drawing. Coupling device 14 is constructed as a snap coupling so that the carrier lance is fixed to it, and after the taking of the sample, upper part 12 of the upper wall with upper cooling body 10, or even the entire sample chamber assembly including lower part 12' of the outer wall and of lower cooling body 7, can be withdrawn upward through carrier tube 1. If the complete sample chamber assembly is withdrawn, inlet tube 2, which is fixed in the lower part of the sample chamber assembly, can also be withdrawn.

Coupling device 14 has a gas flow channel that runs essentially in the longitudinal axis of the coupling device, which can be connected to a source of inert gas via the carrier lance, and through which inert gas can be introduced into hollow space 15 of the sample chamber assembly, so that after removal of upper cooling body 7 from sample cavity 9, the sample is surrounded by inert gas and cannot oxidize. In a known manner, thermal element 3 has, at its end shown only schematically and situated opposite the immersion end, an electrical connector that, likewise in a known manner, can be connected to a carrier lance, so that the electrical signals of the thermal element can be conducted outward to an evaluation device.

Figure 2:
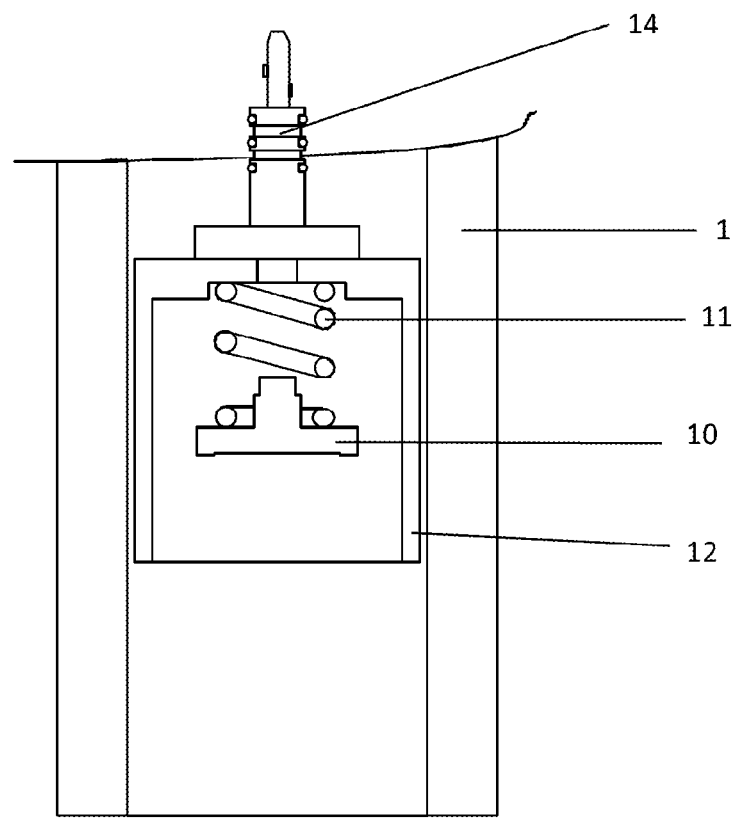
FIG. 2 is an exploded view of parts of the sampler of FIG. 1 after the removal of the sample.
Figure 2:
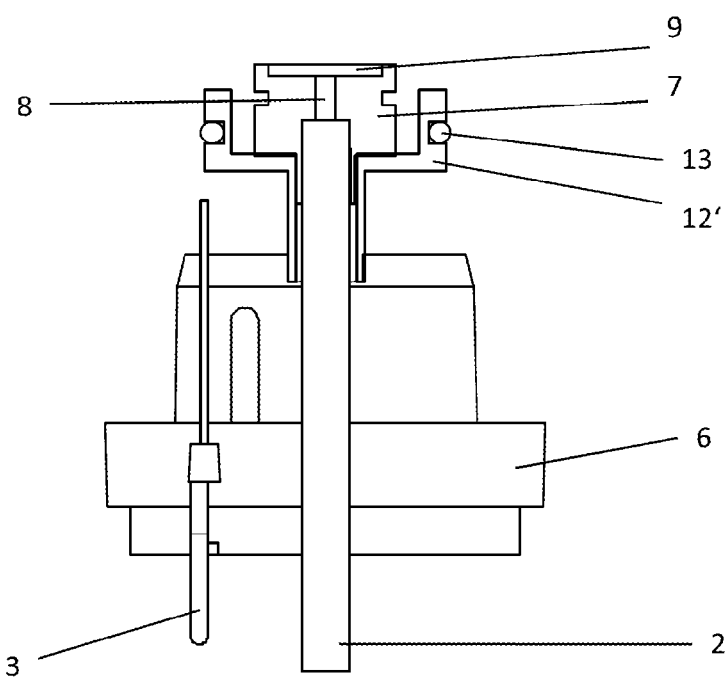
Figure 3:
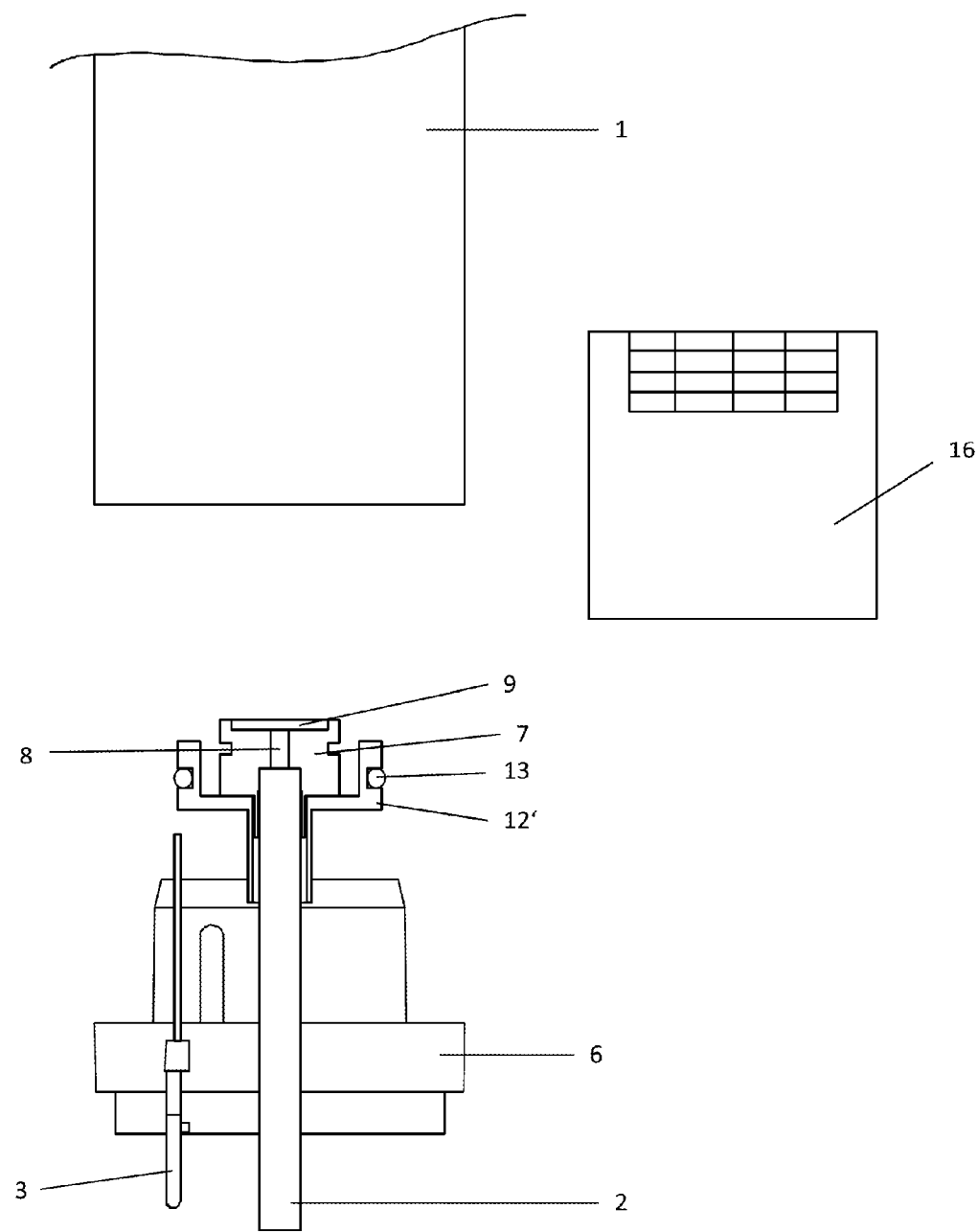
FIG. 3 is a schematic representation of parts of the sampler before an analysis.

FIG. 2 shows the removal of the upper part of the sample chamber assembly with upper part 12 of the outer wall, upper cooling body 10, and spiral spring 11, from the lower part of the sample chamber assembly with sample cavity 9 filled with metal melt, lower cooling body 7, and lower part 12' of the outer wall. After the separation of this lower part from the upper part of the sample chamber assembly, the lower part is withdrawn from the immersion end of carrier tube 1, so that the sample, which is situated in sample cavity 9 and has in the meantime cooled, can be delivered to a spectrometer 16 (see FIG. 3) for analysis.

Figure 4:
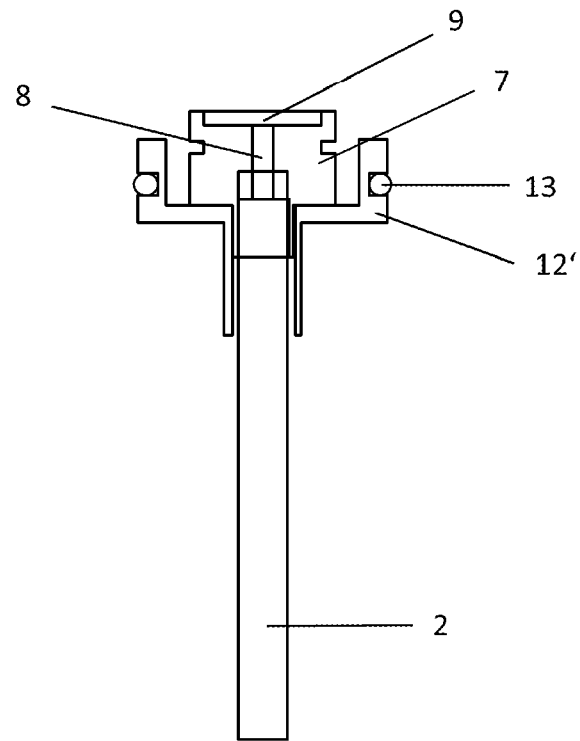
FIG. 4 is a schematic representation of parts of the sample chamber.
Figure 4:
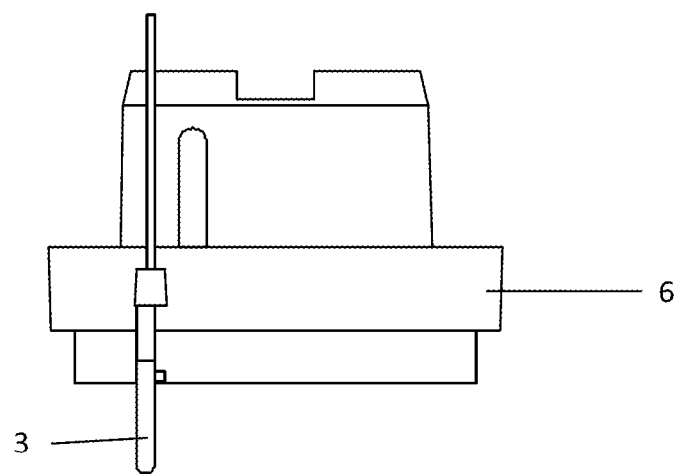

FIG. 4 shows the removal of the lower part of the sample chamber assembly, including inlet tube 2, from refractory body 6.

Figure 5:
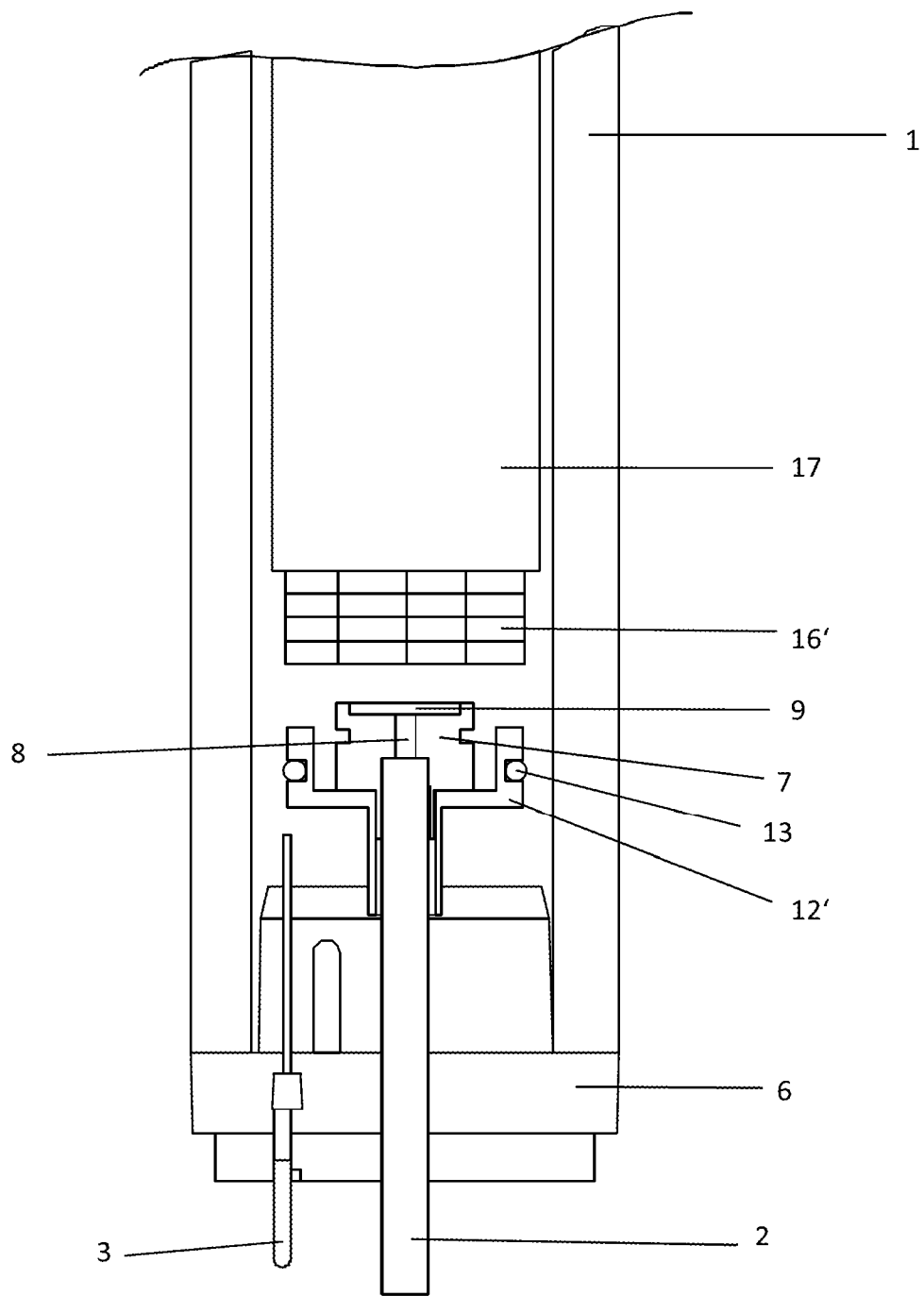
FIG. 5 is a schematic representation showing an analysis inside the carrier tube.

The removal of the upper part of the sample chamber assembly through carrier lance 1 is shown in FIG. 5. Here it is shown that, after the removal of the upper part of the sample chamber assembly and the exposure of the surface of the sample in sample cavity 9, a spectrometer 16' is led through carrier tube 1, with the aid of a spectrometer lance 17, up to sample cavity 9, so that the sample analysis can take place inside carrier tube 1. In this context, the term "sample analysis" refers to the reception of the optical signals necessary for evaluation by spectrometer 16,16; from there the signals are transmitted to evaluation devices, computers, or the like.

Figure 6:
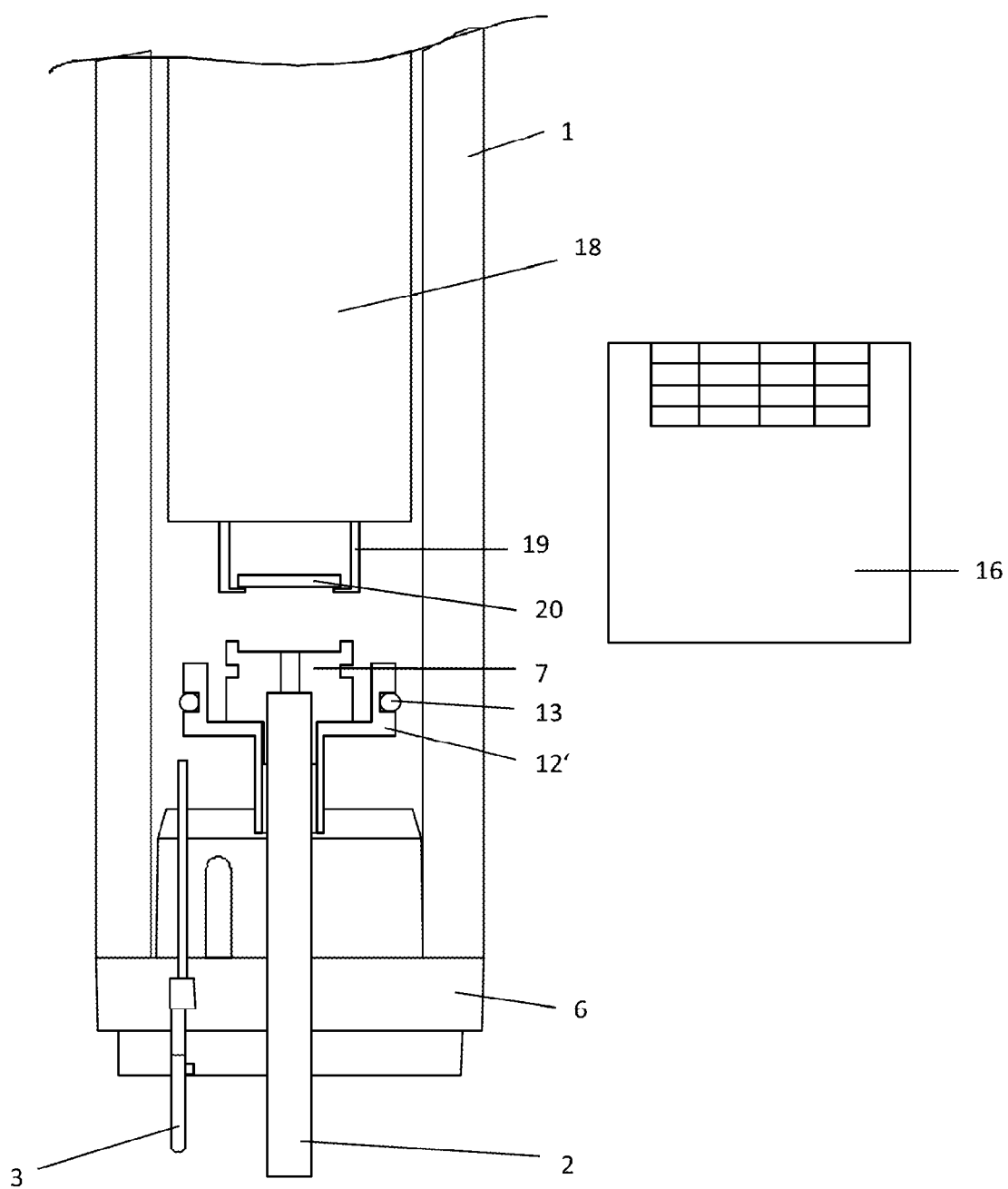
FIG. 6 is a schematic representation showing removal of the sample inside the carrier tube.

FIG. 6 shows a further possibility for sample analysis. Here, differing from the variant shown in FIG. 5, after the removal of the upper part of the sample chamber assembly a gripper lance 18 is introduced into the carrier tube, with the aid of which a gripper 19 can grasp sample 20 and withdraw it through carrier tube 1, so that sample 20 can be delivered to spectrometer 16 with the aid of gripper lance 18.

Figure 7:
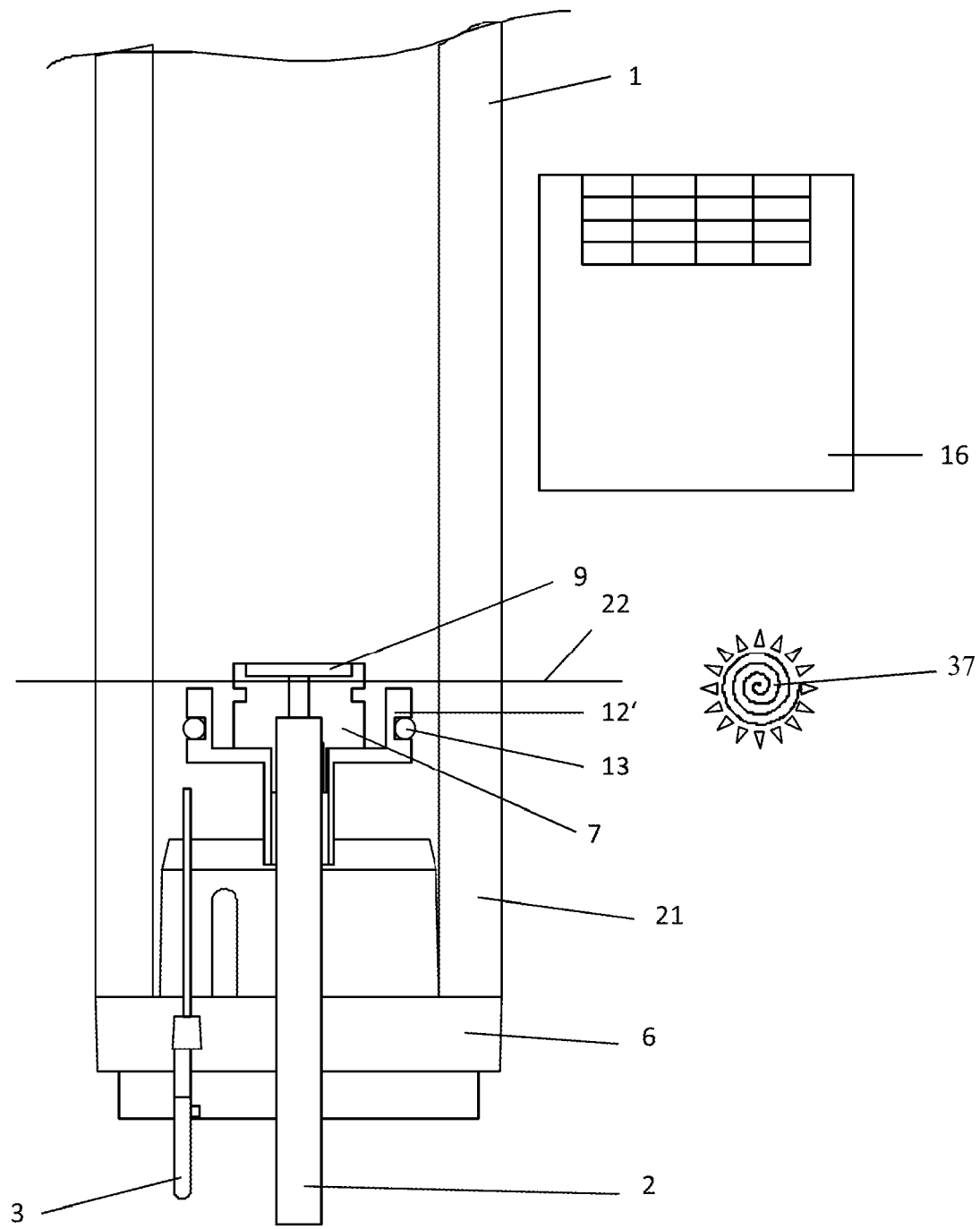
FIG. 7 is a schematic representation showing the preparation for an analysis by separating the immersion end of the sampler.

An alternative to the specific embodiment shown in FIG. 2 is shown in FIG. 7. Instead of downwardly withdrawing the lower part of the sample chamber assembly with refractory body 6 from the immersion end of the carrier tube, after removal of the upper part of the sample chamber assembly through carrier tube 1 using the carrier lance, immersion end 21 of carrier tube 1 can be separated from the rest of carrier tube 1 along marking 22, approximately at the level of sample cavity 9. A conventional cutting tool 37, shown only schematically in FIG. 7, can be used for this purpose. In this case as well, the sample can subsequently be delivered to a spectrometer 16 for analysis.

Instead of cutting off the immersion end, this end can also be destroyed in some other conventional manner, such that the sample can be removed and delivered for analysis. In this case as well, the sample has undergone sufficient cooling by cooling bodies 7,10 before being removed from carrier tube 1. After separation of immersion end 21 and removal of the lower part of the sample chamber, the sample is without more accessible for analysis, whereby the exposure of the sample surface to be analyzed takes place in a "clean" and, if necessary, inert atmosphere.

Figure 8:
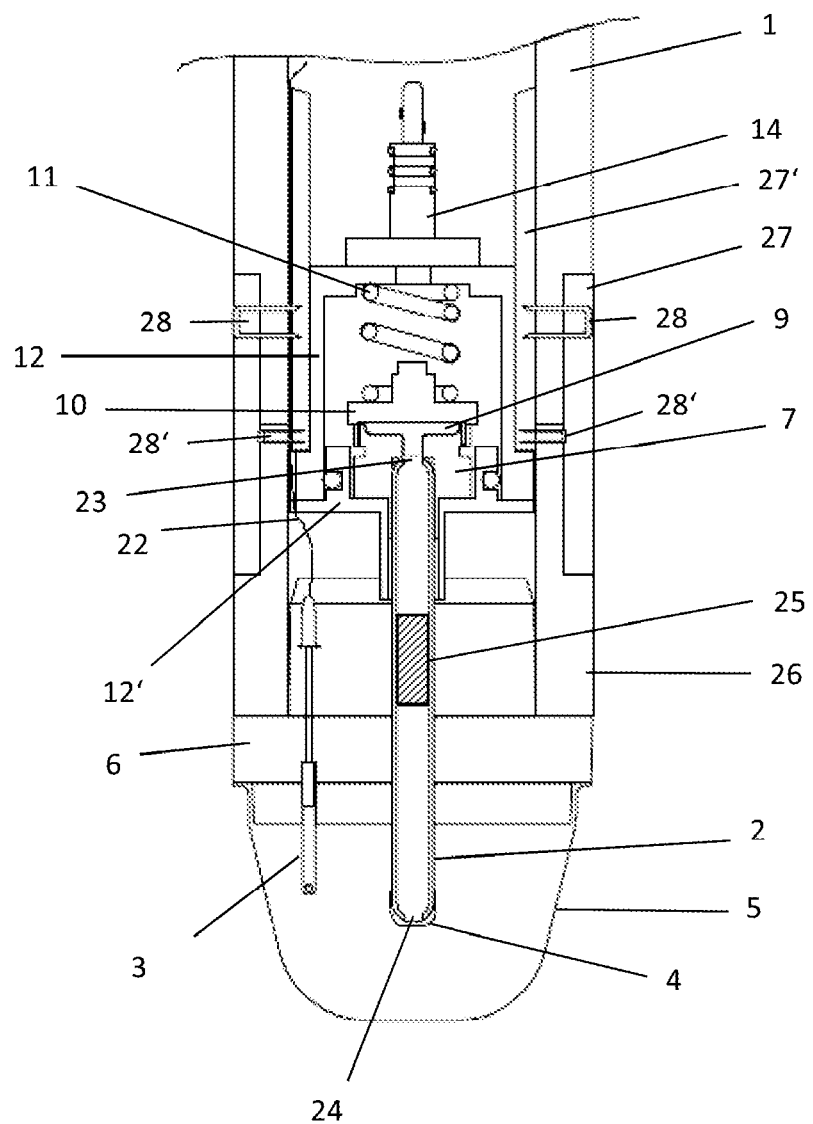
FIG. 8 is a schematic, longitudinal, cross-sectional representation of a sampler according to a further embodiment of the invention.

FIG. 8 shows an embodiment of the sampler that is alternative or preferred to FIG. 1. The sample chamber assembly inside the sampler is constructed in a manner analogous to the specific embodiment shown in FIG. 1. Cooling bodies 7,10 are made of copper. Here, given the relative sizes shown in the Figures, a ratio V of approximately 0.0167 results.

Inlet tube 2 has a diameter of approximately 8 mm, its inlet opening 23 has a diameter of approximately 6 mm, and the opposite opening 24 has a diameter of approximately 3 mm. Aluminum is arranged in inlet tube 2 as de-oxidation agent 25. In addition to inlet tube 2, a thermal element 3 is fixed on refractory body 6, and is connected to a measurement electronics unit by thermal element wires 22.

Carrier tube 1, made of cardboard, has a cardboard tube 26 on its immersion end. This tube is connected to carrier tube 1 by a connecting tube 27, which connects the mutually abutting ends of carrier tube 1 and cardboard tube 26. On its outer circumference, connecting tube 27 terminates approximately flush with carrier tube 1 and with cardboard tube 26. Inside carrier tube 1 there is arranged an inner connecting tube 27', which bridges the connecting point between cardboard tube 26 and carrier tube 1 and, on its inner side, lies against the upper part of outer wall 12 of the sample chamber, and fixes it.

Carrier tube 1, cardboard tube 26, and connecting tubes 27,27' are connected to one another by clamps 28,28'. This connecting point is easily detached through simple mechanical action, so that carrier tube 1 can be removed from cardboard tube 26, whereby the upper part of outer wall 12 of the sample chamber assembly, connected to carrier tube 1 by inner connecting tube 27', remains on carrier tube 1, and the lower part of outer wall 12' is fixed on cardboard tube 26 and remains thereon, so that the two parts of outer wall 12,12' are detached from one another.

Figure 9:
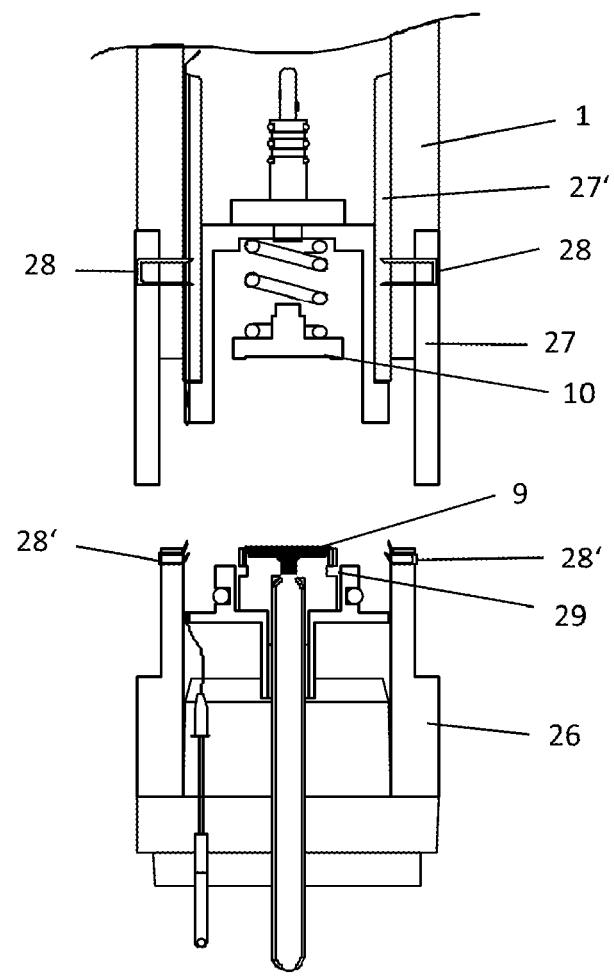
FIG. 9 is an exploded view of parts of the sampler embodiment of FIG. 8 during the removal of the sample from the mold.

Connecting tube 27 is here connected with a larger clamp 28 to carrier tube 1 and to inner connecting tube 27', while cardboard tube 26 is connected to inner connecting tube 27' with smaller clamps 28'. This connection with smaller clamps 28' is, for example, detached by rotation of carrier tube 1 relative to cardboard tube 26, as shown in FIG. 9. Here, the connecting wires of sensors, i.e. thermal element wires 22, are also separated. As is shown in FIG. 9 by example, the separation takes place below the analysis surface of the sample exposed during the separation, i.e. between the analysis surface and the immersion end of the sampler, so that the separated thermal element wires do not come in front of the analysis surface, where they could disturb the analysis.

After the separation, sample cavity 9 with the sample is now accessible to analysis, because cooling body 10 has been removed, and a smooth, flat sample surface is exposed. Openings 29 arranged in lower cooling body 7 connect the sample cavity to hollow space 15 formed between the cooling body 7 of the inner wall and lower part 12' of the outer wall. Excess melt from the sample cavity can exit through these openings 29, which are arranged to open into the circumference of the sample cavity in a uniform circular arrangement, so that samples without bubbles are obtained. The exiting melt hardens and thus holds the sample firmly in this part of the sample chamber assembly, so that the sample with the sample chamber assembly or a part of the sample chamber assembly, namely the lower part facing the immersion end, can be delivered for analysis.

Figure 10:
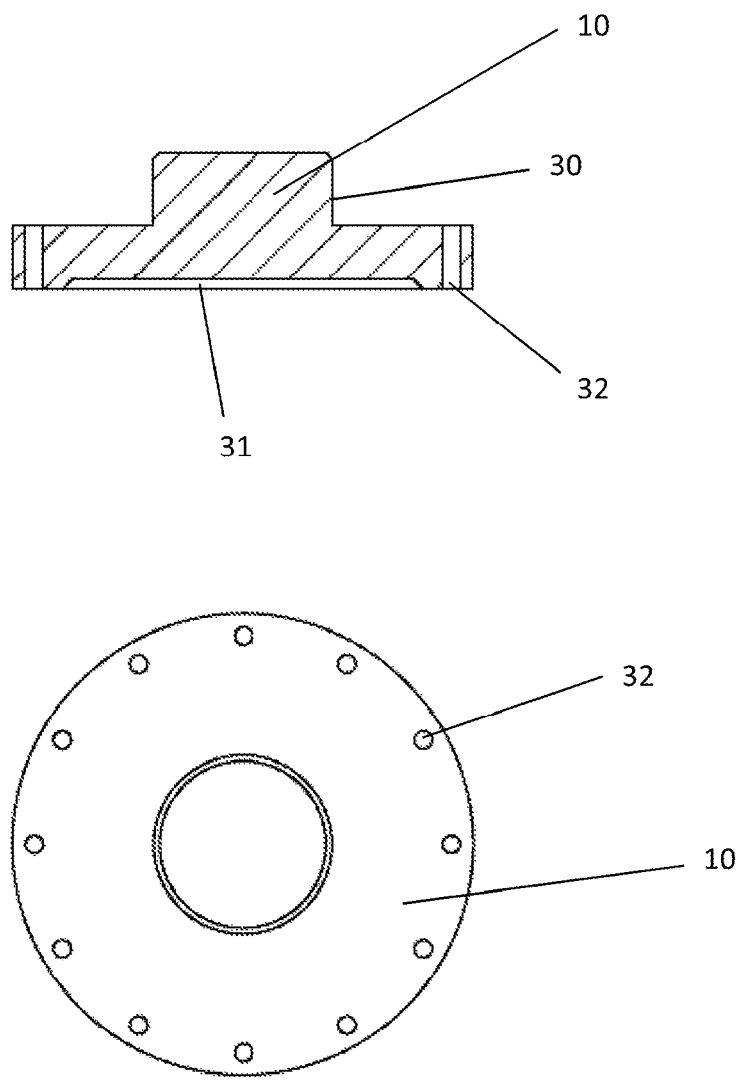
FIG. 10 is a schematic representation of the upper part of the inner wall of the sample chamber assembly in cross-sectional and top views.

FIG. 10 shows upper cooling body 10 in cross-section and, under this, shows it in a top view. On its upper side there is arranged a raised area having an edge 30. Spiral spring 11 is fixed on edge 30. Arranged opposite on the underside of the upper cooling body 10, upper part 31 of sample cavity 9 is shown. Lateral circular ventilation openings 32 are used for gas circulation or for the deliberate supply or discharge of gas from hollow space 15.

Figure 11:
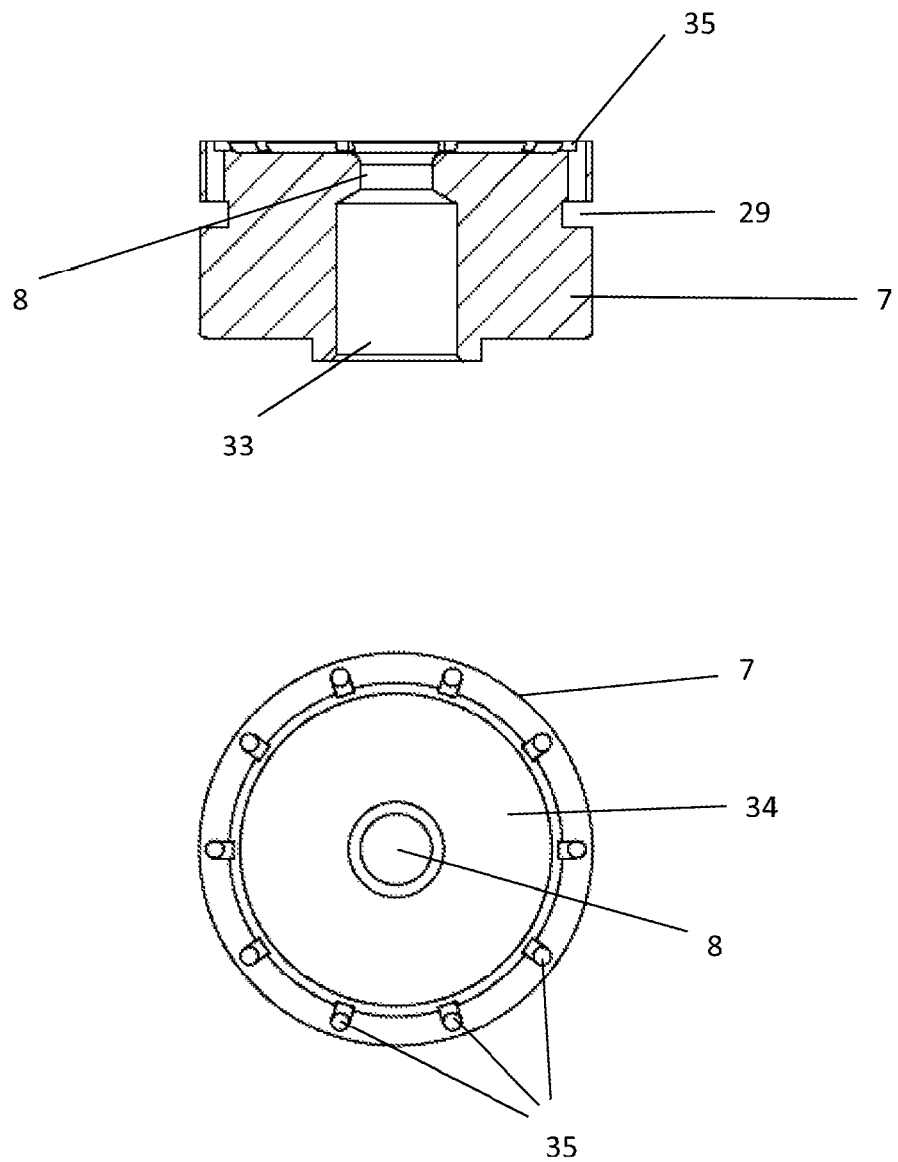
FIG. 11 is a schematic representation of the lower part of the inner wall of the sample chamber assembly in cross-sectional and top views.

FIG. 11 shows lower cooling body 7 in cross-section and, under this, shows it in a top view. In the lower cooling body, there is arranged pass-through opening 8 for metal melts, as well as receptacle 33 for inlet tube 2. Gases can escape from sample cavity 9 through ventilation openings 35 before or during the taking of the sample. Ventilation openings 35 are connected to openings 29 through which excess metal can exit from lower part 34 of the sample cavity.

The ratio of volume (in $mm^3$) of the sample cavity to the overall cross-section (in $mm^2$) of the openings used for ventilation (i.e., ventilation openings 32,35), in the configurations shown as examples in the Figures, is approximately 72 mm, wherein the volume of sample cavity 9 is approximately 1230 $mm^3$ and the overall cross-section of ventilation openings 32,35 is approximately 17 $mm^2$.

Figure 12:
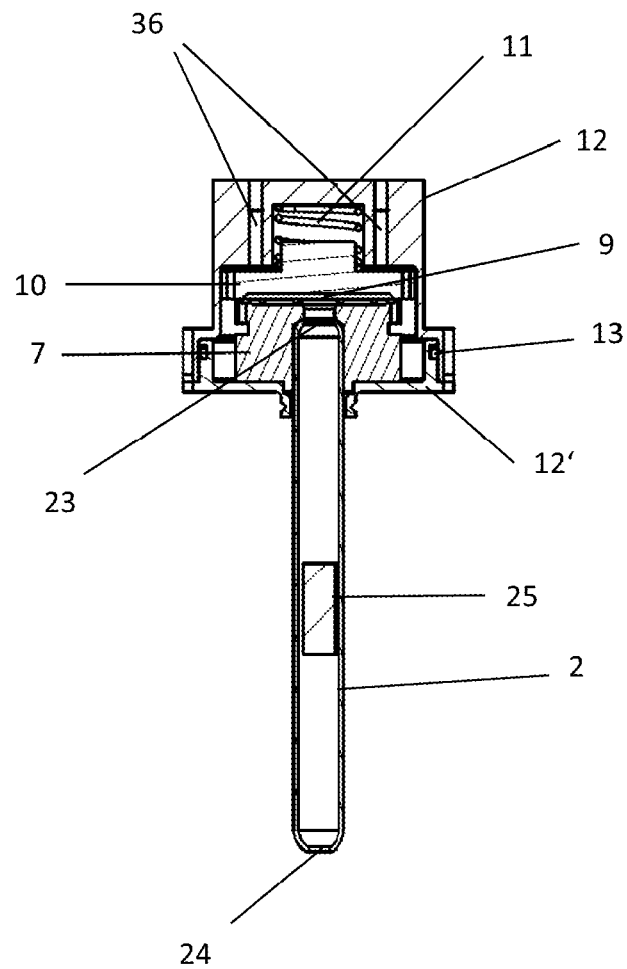
FIG. 12 is a schematic, cross-sectional view of the sample chamber assembly with inner and outer wall.
Figure 13:
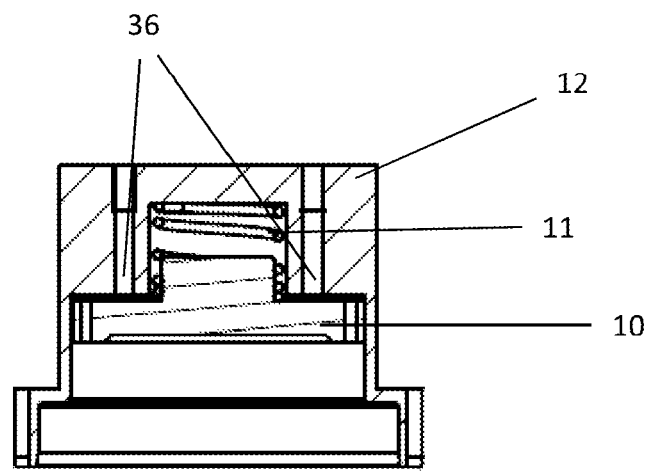
FIG. 13 is a schematic, cross-sectional view of the sample chamber assembly, removed from the mold, with inner and outer wall.
Figure 13:
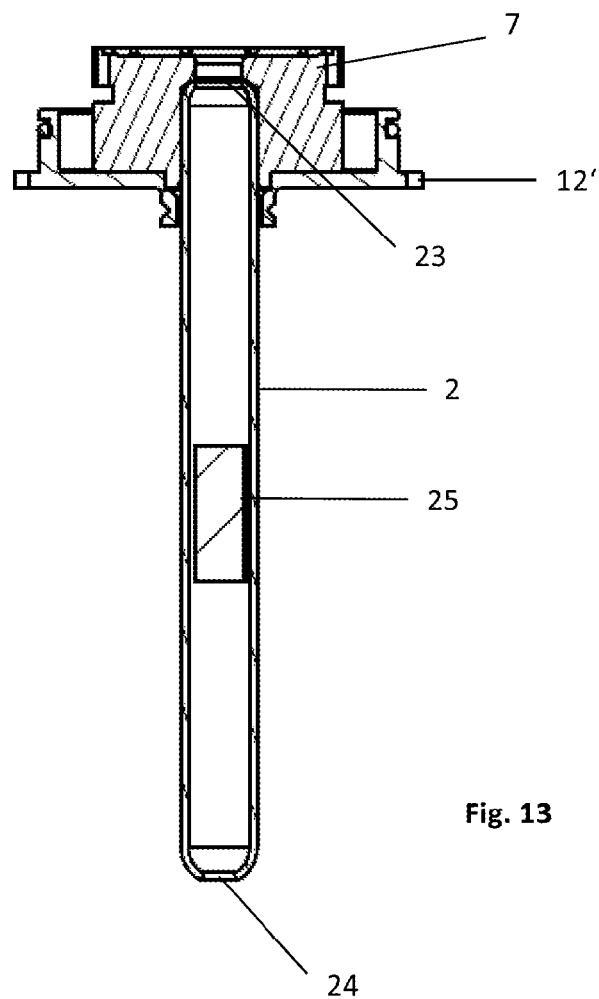

FIGS. 12 and 13 show the sample chamber assembly with inner and outer wall, in the assembled state (FIG. 12) and in the state removed from the mold (FIG. 13). Upper part 12 and lower part 12' of the outer wall are made of aluminum. They grasp cooling bodies 7,10, which are pressed together by a spiral spring 11 and surround sample cavity 9. Clearly visible is inlet tube 2 with its two ends having reduced diameter, inlet opening 23 and opposite opening 24. Also shown are gas flow channels 36 of upper part 12 of the outer wall.

The examples do not limit the invention; in particular, features of a specific embodiment that do not directly interact functionally are also transferable to other specifically or generally described specific embodiments of the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I/we claim:

1. A sampler for taking samples from a melt having a melting point higher than 600° C., particularly a metal or cryolite melt, the sampler comprising:
    a carrier tube having an immersion end;
    a sample chamber assembly arranged on the immersion end of the carrier tube and at least partially inside the carrier tube, the sample chamber assembly having:
        an inlet opening;
        an inner wall forming a sample cavity for receiving the melt, and
        an outer wall which surrounds the inner wall at least partially at a distance therefrom, such that a hollow space is arranged between the outer wall and the inner wall; and
    a coupling device arranged on a part of an outer surface of the sample chamber assembly, the coupling device being arranged inside the carrier tube for coupling a carrier lance thereto,
        wherein, when the sample cavity is filled with a sample of the melt, a ratio of a mass of the melt accommodated in the sample cavity to a mass of the sample chamber assembly without the melt is less than 0.8.

2. The sampler according to claim 1, wherein the sample chamber assembly has a plurality of parts that directly surround the sample cavity and are detachable from one another, and wherein at least one of the parts is arranged inside the carrier tube.

3. The sampler according to claim 2, wherein the sample chamber assembly has a first part and a second part that together surround the sample cavity, wherein the carrier tube has a main part containing the coupling device and an end part arranged at the immersion end of the carrier tube and detachable from the main part, and wherein the first part of the sample chamber assembly is fixed on the main part and the second part of the sample chamber assembly is fixed on the end part of the carrier tube.

4. The sampler according to claim 3, wherein the end part is connected to the main part by a press-fit connection or screwed connection.

5. The sampler according to claim 3, wherein the end part is connected to the main part by clamps or staples.

6. The sampler according to claim 1, wherein the sample chamber assembly or the part of the outer surface of the sample chamber assembly having the coupling device is arranged on the immersion end of the carrier tube, such that the sample chamber assembly or the part of the outer surface having the coupling device is movable through an interior of the carrier tube to an end of the carrier tube opposite the immersion end and is there movable out of the carrier tube.

7. The sampler according to claim 6, wherein the sample chamber assembly or the part of the outer surface of the sample chamber assembly having the coupling device has a cross-section perpendicular to the longitudinal axis of the carrier tube, which cross-section is no larger than a cross-section of the interior of the carrier tube perpendicular to its longitudinal axis.

8. The sampler according to claim 1, wherein the coupling device is constructed as at least one of a snap coupling, a bayonet coupling, and a screw coupling.

9. The sampler according to claim 1, wherein the ratio of the mass of the melt accommodated in the sample cavity to the mass of the sample chamber assembly without the melt is at most 0.1.

10. The sampler according to claim 1, wherein the coupling device has at least one gas flow channel which runs through the outer wall of the sample chamber assembly or leads up to the outer wall.

11. A sample chamber assembly for a sampler according to claim 1,
wherein the sample cavity is directly surrounded by the inner wall, the inner wall being formed of a plurality of parts,
wherein an inlet tube is connected to the sample cavity for accommodating a sample of a metal melt or cryolite melt in the sample cavity,
wherein the inlet tube opens into the sample cavity with the inlet opening, and
wherein, when the sample cavity is filled with the sample of a metal melt or cryolite melt, a ratio V between mass M of the sample and mass m of material of the inner wall is represented by the following equation:

$$V = \frac{M \times 24000}{m \times c \times \lambda} < 0.15$$

where m is the mass of the inner wall, c is the specific heat capacity of the material of the inner wall, and $\lambda$ is the thermal conductivity of the material of the inner wall.

12. The sample chamber assembly according to claim 11, wherein V<0.05.

13. The sample chamber assembly according to claim 11, wherein a volume of the sample cavity divided by an overall cross-sectional area of openings serving for ventilation is less than 500 mm.

14. The sample chamber assembly according to claim 13, wherein the volume of the sample cavity divided by the overall cross-sectional of the openings serving for ventilation is less than 100 mm.

15. The sample chamber assembly according to claim 11, wherein the sample chamber assembly has at least two parts immediately surrounding the sample cavity and detachable from one another.

16. The sample chamber assembly according to claim 11, wherein the inlet tube has a reduced cross-section at the inlet opening.

17. A method for taking samples from a melt having a melt temperature greater than 600° C., particularly a metal or cryolite melt, using a sampler comprising a carrier tube having an immersion end, a sample chamber assembly arranged on the immersion end of the carrier tube and at least partially inside the carrier tube, and a coupling device arranged on a part of an outer surface of the sample chamber assembly, the coupling device being arranged inside the carrier tube for coupling a carrier lance thereto, the sample chamber assembly having an inlet opening, an inner wall forming a sample cavity for receiving the melt, and an outer wall which surrounds the inner wall at least partially at a distance therefrom, such that a hollow space is arranged between the outer wall and the inner wall the sample chamber assembly;
the method comprising pushing a carrier lance into the carrier tube through an end opposite the immersion end of the carrier tube, coupling the carrier lance to the coupling device of the sample chamber assembly, subsequently immersing the immersion end of the carrier tube in the melt, such that the sample cavity of the sample chamber assembly is filled with the melt, then pulling the sample chamber assembly or the part of the sample chamber assembly having the coupling device through the carrier tube using the carrier lance, withdrawing the sample chamber assembly or the part of the sample chamber assembly having the coupling device from the end of the carrier tube opposite the immersion end, wherein after the withdrawal a part of a surface of the sample situated in the sample chamber assembly enters into immediate contact with a surrounding environment of the sample chamber assembly, pushing a lance having a spectrometer into the carrier tube, and analyzing the surface of the sample with the aid of the spectrometer.

18. The method according to claim 17, wherein during and/or after the taking of the sample, an inert gas is conducted to the sample chamber assembly or into a hollow space of the sample chamber assembly.

19. A method for taking samples from a melt having a melt temperature greater than 600° C., particularly a metal or cryolite melt, using a sampler comprising a carrier tube having an immersion end, a sample chamber assembly arranged on the immersion end of the carrier tube and at least partially inside the carrier tube, and a coupling device arranged on a part of an outer surface of the sample chamber assembly, the coupling device being arranged inside the carrier tube for coupling a carrier lance thereto, the sample chamber assembly having an inlet opening, an inner wall forming a sample cavity for receiving the melt, and an outer wall which surrounds the inner wall at least partially at a distance therefrom, such that a hollow space is arranged between the outer wall and the inner wall the sample chamber assembly;
the method comprising pushing a carrier lance into the carrier tube through an end opposite the immersion end of the carrier tube, coupling the carrier lance to the coupling device of the sample chamber assembly, subsequently immersing the immersion end of the carrier tube in the melt, such that the sample cavity of the sample chamber assembly is filled with the melt, subsequently pulling the sample chamber assembly or the part of the outer surface of the sample chamber assembly having the coupling device through the carrier tube using the carrier lance, withdrawing the sample chamber assembly or the part of the sample chamber assembly having the coupling device from the end of the carrier tube opposite the immersion end, wherein after the withdrawal a part of a surface of the sample situated in the sample chamber assembly enters into immediate contact with a surrounding environment of the sample chamber assembly, pushing a lance having a gripper into the carrier tube, grasping the sample with the gripper, removing the sample from the sample chamber assembly, pulls the sample through the carrier tube, and withdrawing the sample from the end of the carrier tube opposite the immersion end.

20. The method according to claim 19, wherein after the withdrawal from the carrier tube the sample is delivered to an analysis device.

\* \* \* \* \*